US00PP26896P3

(12) United States Plant Patent
Danziger

(10) Patent No.: US PP26,896 P3
(45) Date of Patent: Jun. 28, 2016

(54) ***SUTERA* PLANT NAMED 'DANCOP103'**

(50) Latin Name: *Sutera cordata*
Varietal Denomination: DANCOP103

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 126 days.

(21) Appl. No.: 13/999,860

(22) Filed: Mar. 28, 2014

(65) Prior Publication Data

US 2015/0282417 P1 Oct. 1, 2015

(51) Int. Cl.
*A01H 5/02* (2006.01)

(52) U.S. Cl.
USPC ..... Plt./485

(58) Field of Classification Search
USPC ..... Plt./485
See application file for complete search history.

*Primary Examiner* — Keith Robinson
(74) *Attorney, Agent, or Firm* — Cassandra Bright

(57) ABSTRACT

A new and distinct *Sutera* cultivar named 'DANCOP103' is disclosed, characterized by early and abundant extra large white flowers, a mounded, very compact habit, very well branched form and medium vigor. The new variety is a *Sutera*, normally produced as an outdoor garden or container plant.

2 Drawing Sheets

Figure 1:
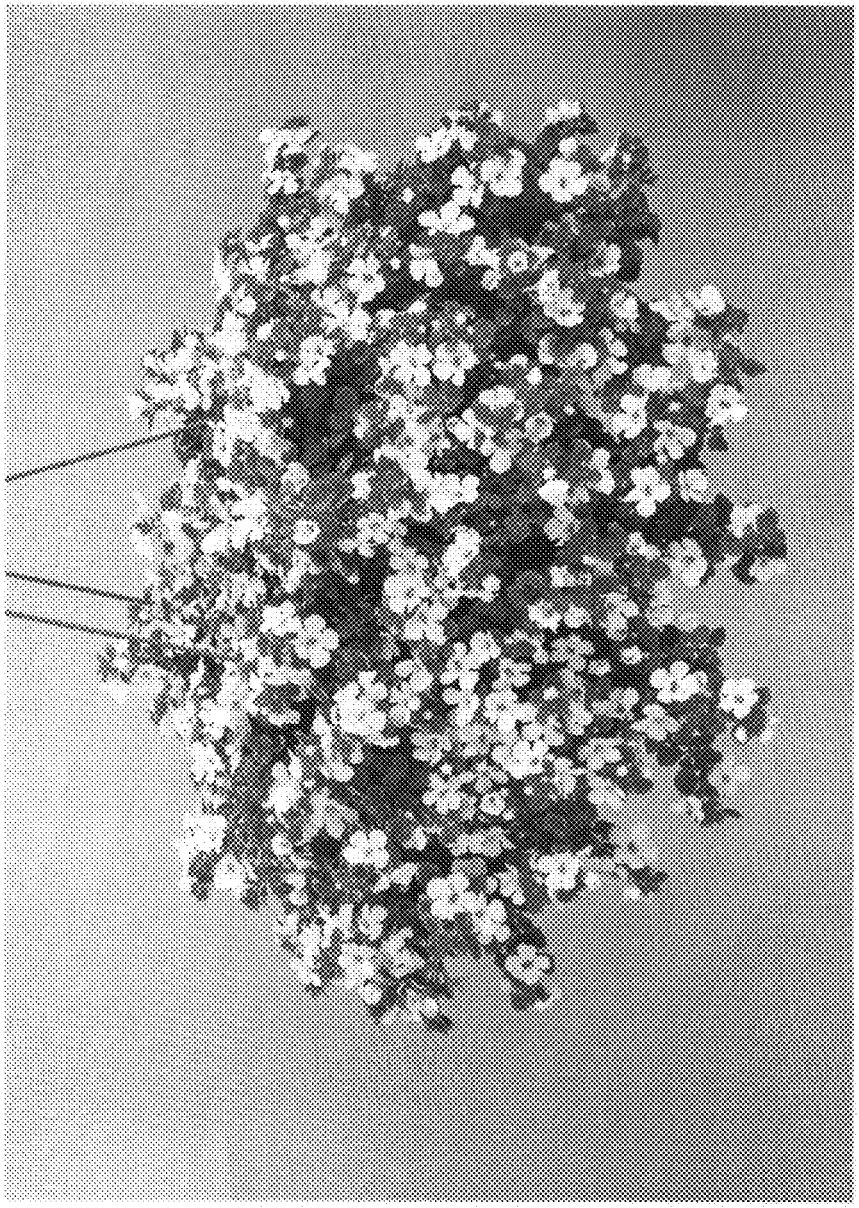

Latin name of the genus and species: *Sutera cordata.*
Variety denomination: 'DANCOP103'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The cross resulting in this new variety was made during March of 2009.

The seed parent is the unpatented, proprietary seedling variety referred to as *Sutera cordata* 'cv. 09-1202' The pollen parent is unknown as the new variety is the result of an open pollination breeding program. The new variety was discovered in November of 2010 by the inventor in a group of seedlings resulting from the 2009 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during December of 2010 and has shown that the unique features of this cultivar are stable and reproduced true to type in more than 20 successive generations.

SUMMARY OF THE INVENTION

The cultivar 'DANCOP103' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANCOP103' These characteristics in combination distinguish 'DANCOP103' as a new and distinct *Sutera* cultivar:

1. Mounded, very compact growth habit.
2. Extra large white flowers.

3. Very branched.
4. Early, abundant flowering.
5. Medium vigor.

Plants of the new cultivar 'DANCOP103' are similar to plants of the seed parent, *Sutera cordata* 'cv. 09-1202' in most horticultural characteristics, however, plants of the new cultivar 'DANCOP103' differs in the following ways:

1. Parent variety has a semi-trailing, elongated growth habit.
2. Parent variety has smaller white flowers.
3. Seed parent has less branching.
4. Seed parent begins flowering late, with a medium quantity flowering.
5. Parent variety grows more vigorously.

COMMERCIAL COMPARISON

Plants of the new cultivar 'DANCOP103' are comparable to the commercial variety *Sutera* 'DANCOP25' U.S. Plant Pat. No. 19,747. The two *Sutera* varieties are similar in most horticultural characteristics; however, the new variety 'DANCOP103' differs in the following ways:

1. Comparison variety has elongated, semi-trailing growth habit whereas candidate variety has mounded, very compact growth habit.
2. Comparison variety has white flowers, larger than those of the new variety.
3. Comparison variety has medium branching whereas candidate variety is very well branched.
4. Comparison variety plant height is shorter than the height of the new variety.
5. Comparison variety has strong vigor whereas candidate variety has medium vigor.

Plants of the new cultivar 'DANCOP103' are also comparable to the unpatented commercial variety *Sutera* 'Scopia Great White Improved'. The two *Sutera* varieties are similar in most horticultural characteristics; however, the new variety 'DANCOP103' differs in the following ways:

1. Comparison variety has semi-trailing, elongated growth habit whereas candidate variety has mounded, very compact growth habit.
2. Comparison variety has large, white flowers whereas candidate variety has extra-large flowers.
3 Candidate variety is more branched than comparison variety.
4. Comparison variety does not bloom as early as candidate variety, and flowering of comparison variety is not as abundant as candidate variety.
5. Comparison variety has strong vigor whereas candidate variety has medium vigor.

BRIEF DESCRIPTION OF THE PHOTOGRAPHS

The accompanying photograph in FIG. 1 illustrates in full color a typical plant of 'DANCOP103' grown in a greenhouse, in a 13 cm pot. Age of the plant photographed is approximately 3 months old from rooted cutting.

Figure 2:
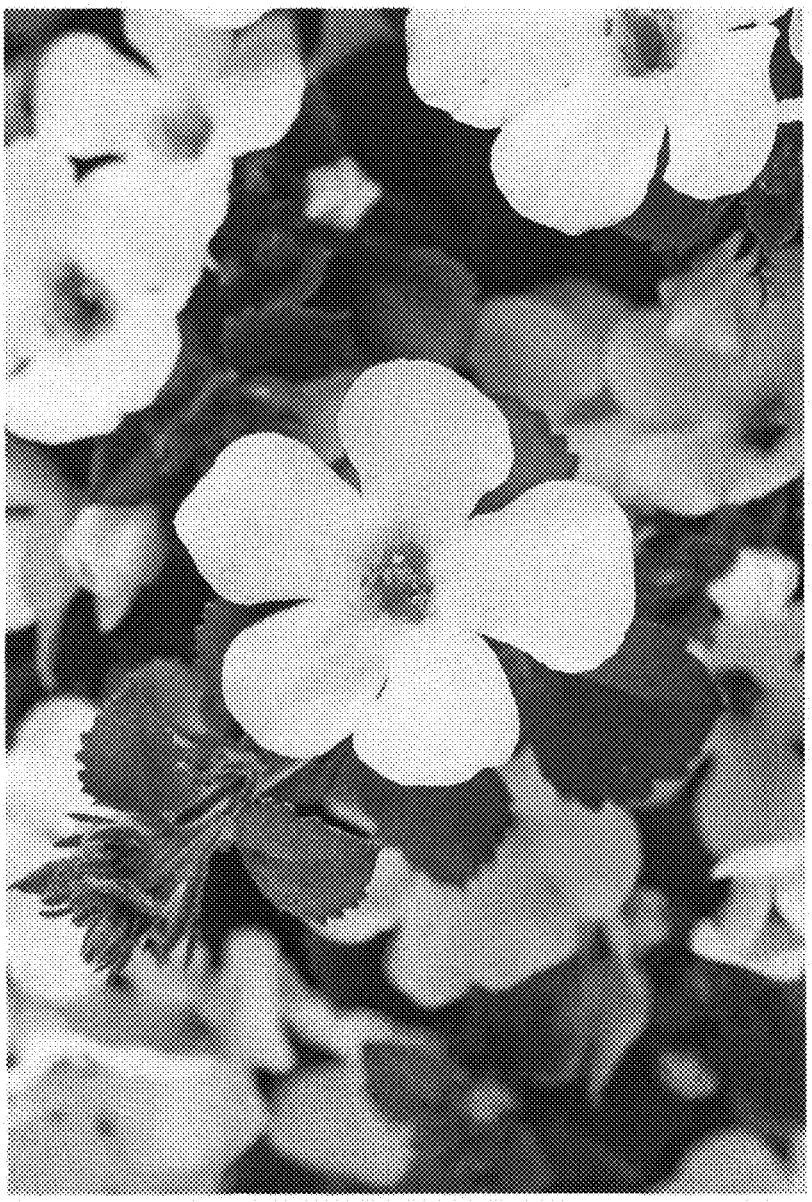

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DANCOP103' plants grown in a greenhouse during Winter to Spring in Moshav Mishmar Hashiva, Israel. The growing temperature ranged from 15° C. to 26° C. during the day and from 13° C. to 16° C. during the night. Measurements and numerical values represent averages of typical plant types.

Botanical classification: *Sutera cordata* 'DANCOP103'.

PROPAGATION

Typical propagation material: Vegetative cuttings.
Time to rooting: 7 to 10 days at approximately 20° C.
Root description: Fine, fibrous roots.
Root color: Near RHS Orange-White 159C and 159D.

PLANT

Age of plant described: Approximately 3 months old.
Pot size of plant described: 13 cm.
Height: About 16 cm.
Plant spread: About 45 cm.
Growth rate: Medium.
Branching characteristics:
Length of primary lateral branches: About 20 cm.
Diameter of lateral branches: About 0.2 cm.
Quantity of primary lateral branches: About 12.
Characteristics of primary lateral branches:
- *Form*.—Cylindrical.
- *Diameter*.—About 0.2 cm.
- *Color*.—RHS Green 137 B.
- *Texture*.—Velvety.
- *Strength*.—Strong.

Internode length: About 1.5 cm.

FOLIAGE

Leaf:
- *Arrangement*.—Opposite, petiolate.
- *Quantity*.—Approximately 40 per branch.
- *Average length*.—2.5 cm.
- *Average width*.—2.2 cm.
- *Shape of blade*.—Ovate.
- *Apex*.—Obtuse.
- *Base*.—Acuminate.
- *Margin*.—Serrate.
- *Texture of top surface*.—Velvety, Slightly pubescent.
- *Texture of bottom surface*.—Velvety, Slightly pubescent.
- *Aspect*.—About 90° to the branch.
- *Color*.—Unvariegated. Young foliage upper side: RHS Green 137 C. Young foliage under side: RHS Green 137 D. Mature foliage upper side: RHS Green 137 A. Mature foliage under side: RHS Green 137 B.
- *Venation*.—Type: Pinnate. Venation color upper side: RHS Green 137 A. Venation color under side: RHS Green 137 B.
- *Petiole*.—Length: About 0.3 cm. Diameter: About 0.2 cm. Color: RHS Green 137 A. Texture: Slightly velvety.

FLOWER

Natural flowering season: All year round.
Days to flowering from rooted cutting: About 45.
Inflorescence and flower type and habit: Axillary, solitary salverform single flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.6 cm.
- *Diameter*.—About 0.7 cm.
- *Color*.—RHS White 155 C.

Flower size:
- *Diameter*.—About 2.6 cm.
- *Length*.—About 1.5 cm.
- *Corolla tube diameter*.—About 0.4 cm.
- *Corolla tube length*.—About 1.2. cm.

Corolla/petals:
- *Arrangement*.—Symmetric.
- *Lobe length*.—About 1.0 cm.
- *Lobe width*.—About 0.9 cm.
- *Quantity*.—5.
- *Texture*.—Velvety.
- *Lobe apex*.—Rounded.
- *Lobe shape*.—Rounded.
- *Margin*.—Entire.
- *Aspect*.—About 90° to the tube.

Color:
- *When opening*.—Upper surface: RHS White 155 C. Lower surface: RHS White 155 C.
- *Fully opened*.—Upper surface: RHS. White 155 C. Lower surface: RHS White 155 C.
- *Visible corolla tube color*.—RHS Yellow 13 A.

Calyx/sepals:
*Quantity per flower.*—5.
*Shape*.—Linear.
*Length*.—About 0.6 cm.
*Width*.—About 0.1 cm.
*Apex*.—Acute.
*Base*.—Fused.
*Margin*.—Entire.
*Texture*.—Slightly velvety.
*Color*.—Upper Surface: RHS Green 137 B. Lower Surface: RHS Green 137 C.
Peduncle: None.
Pedicel:
*Length*.—Approximately 1.0 cm.
*Diameter*.—Approximately 0.1 cm.
*Color*.—Near RHS Green 137 C.
*Orientation*.—Slanted upward and outward.
*Pubescence*.—Slightly pubescent.
*Strength*.—Moderately strong, flexible.
Fragrance: None

REPRODUCTIVE ORGANS

Stamens:
*Number.*—4.
*Filament length*.—Approximately 1 cm.
Anthers:
*Shape*.—Cylindrical.
*Length*.—Approximately 0.1 cm.
*Color*.—RHS Yellow 13 B.
*Pollen*.—Color: RHS Yellow-Orange 17 B. Quantity: Sparse.
Pistil:
*Number.*—1.
*Length*.—About 1.1 cm.
*Style*.—Length: About 0.9 cm. Color: RHS Yellow-Green 145 B.
*Stigma*.—Shape: Undulate. Color: RHS Yellow-Green 146 C. Ovary Color: RHS Green 143 B.

OTHER CHARACTERISTICS

Seeds and fruits: About 20 elliptic, small (1mm long) near Grey-Brown 199C seeds per one elliptic brown capsule. Capsules near Brown 200D.
Disease/pest resistance: Typical to known *Sutera* varieties.
Temperature tolerance: The new variety tolerates temperatures between 5 to 40° C.
What is claimed is:
1. A new and distinct cultivar of *Sutera* plant named 'DANCOP103' as herein illustrated and described.

* * * * *